United States Patent
Rioux

(10) Patent No.: US 9,414,883 B2
(45) Date of Patent: Aug. 16, 2016

(54) CO-ACCESS FOAM/ELECTRODE INTRODUCER

(75) Inventor: Robert F. Rioux, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2570 days.

(21) Appl. No.: 11/423,420

(22) Filed: Jun. 9, 2006

(65) Prior Publication Data

US 2007/0287996 A1    Dec. 13, 2007

(51) Int. Cl.
*A61B 18/14* (2006.01)
*A61B 18/00* (2006.01)

(52) U.S. Cl.
CPC ... *A61B 18/1477* (2013.01); *A61B 2018/00214* (2013.01); *A61B 2018/1465* (2013.01); *A61B 2018/1472* (2013.01); *A61B 2018/1475* (2013.01)

(58) Field of Classification Search
CPC ........... A61B 2018/00214; A61B 2018/00577; A61B 2018/1465; A61B 2018/1472; A61B 2018/1475; A61B 18/1477
USPC ................................................ 606/41, 45–47
See application file for complete search history.

(56) References Cited

U.S. PATENT DOCUMENTS

| | | | |
|---|---|---|---|
| 5,007,895 A * | 4/1991 | Burnett | 604/11 |
| 5,713,942 A | 2/1998 | Stern et al. | |
| 5,827,273 A | 10/1998 | Edwards | |
| 5,895,417 A | 4/1999 | Pomeranz et al. | |
| 6,024,743 A | 2/2000 | Edwards | |
| 6,032,077 A | 2/2000 | Pomeranz | |
| 6,119,041 A | 9/2000 | Pomeranz et al. | |
| 6,379,353 B1 | 4/2002 | Nichols | |
| 6,471,659 B2 | 10/2002 | Eggers et al. | |
| 6,579,288 B1 * | 6/2003 | Swanson et al. | 606/41 |
| 6,602,218 B2 * | 8/2003 | Yoon | 604/1 |
| 6,708,056 B2 | 3/2004 | Duchon | |
| 6,736,811 B2 | 5/2004 | Panescu et al. | |
| 6,954,977 B2 | 10/2005 | Maguire et al. | |
| 2003/0040743 A1 * | 2/2003 | Cosman et al. | 606/41 |
| 2003/0078573 A1 | 4/2003 | Truckal | |

(Continued)

FOREIGN PATENT DOCUMENTS

| | | |
|---|---|---|
| DE | 4007295 A1 | 9/1991 |
| EP | 1169972 | 1/2002 |

(Continued)

OTHER PUBLICATIONS

PCT International Search Report for PCT/US2006/027079, Applicant: Boston Scientific Scimed, Inc., Form PCT/ISA/210 and 220, dated Dec. 18, 2006 (6 pages).

(Continued)

*Primary Examiner* — Michael Peffley
*Assistant Examiner* — Samantha Good

(57) ABSTRACT

Methods, medical probe kits, and systems are provided for treating a tissue region within a patient, e.g., a margin of tissue surrounding an interstitial space created by removing abnormal tissue. A delivery cannula is introduced within the patient. A hydrophilic electrode is advanced through the cannula adjacent the tissue region, e.g., within the interstitial cavity. An ablation probe is advanced though the cannula into contact with the hydrophilic electrode, and ablation energy is conveyed from the ablation probe into the tissue region via the hydrophilic electrode.

22 Claims, 8 Drawing Sheets

(56) References Cited

U.S. PATENT DOCUMENTS

| | | |
|---|---|---|
| 2003/0093069 A1 | 5/2003 | Panescu et al. |
| 2004/0098030 A1 | 5/2004 | Makower et al. |
| 2004/0254625 A1 | 12/2004 | Stephens et al. |
| 2005/0015049 A1 | 1/2005 | Rioux et al. |
| 2005/0234443 A1 | 10/2005 | Rioux et al. |
| 2006/0149226 A1 | 7/2006 | McCullagh et al. |

FOREIGN PATENT DOCUMENTS

| | | |
|---|---|---|
| WO | WO 92/10142 | 6/1992 |
| WO | WO 96/00041 | 1/1996 |
| WO | WO 96/07360 | 3/1996 |
| WO | WO 00/09208 | 2/2000 |
| WO | WO 02/087453 | 11/2002 |
| WO | WO 03/034932 | 5/2003 |

OTHER PUBLICATIONS

PCT Written Opinion for the International Search Report for PCT/US2006/027079, Applicant: Boston Scientific Scimed, Inc., Form PCT/ISA/237, dated Dec. 18, 2006 (6 pages).

PCT International Preliminary Report on Patentability (Chapter I of the Patent Cooperation Treaty) for PCT/US2006/027079, Applicant: Boston Scientific Scimed, Inc., Form PCT/IB/326 and 373, dated Jan. 22, 2008 (7 pages).

* cited by examiner

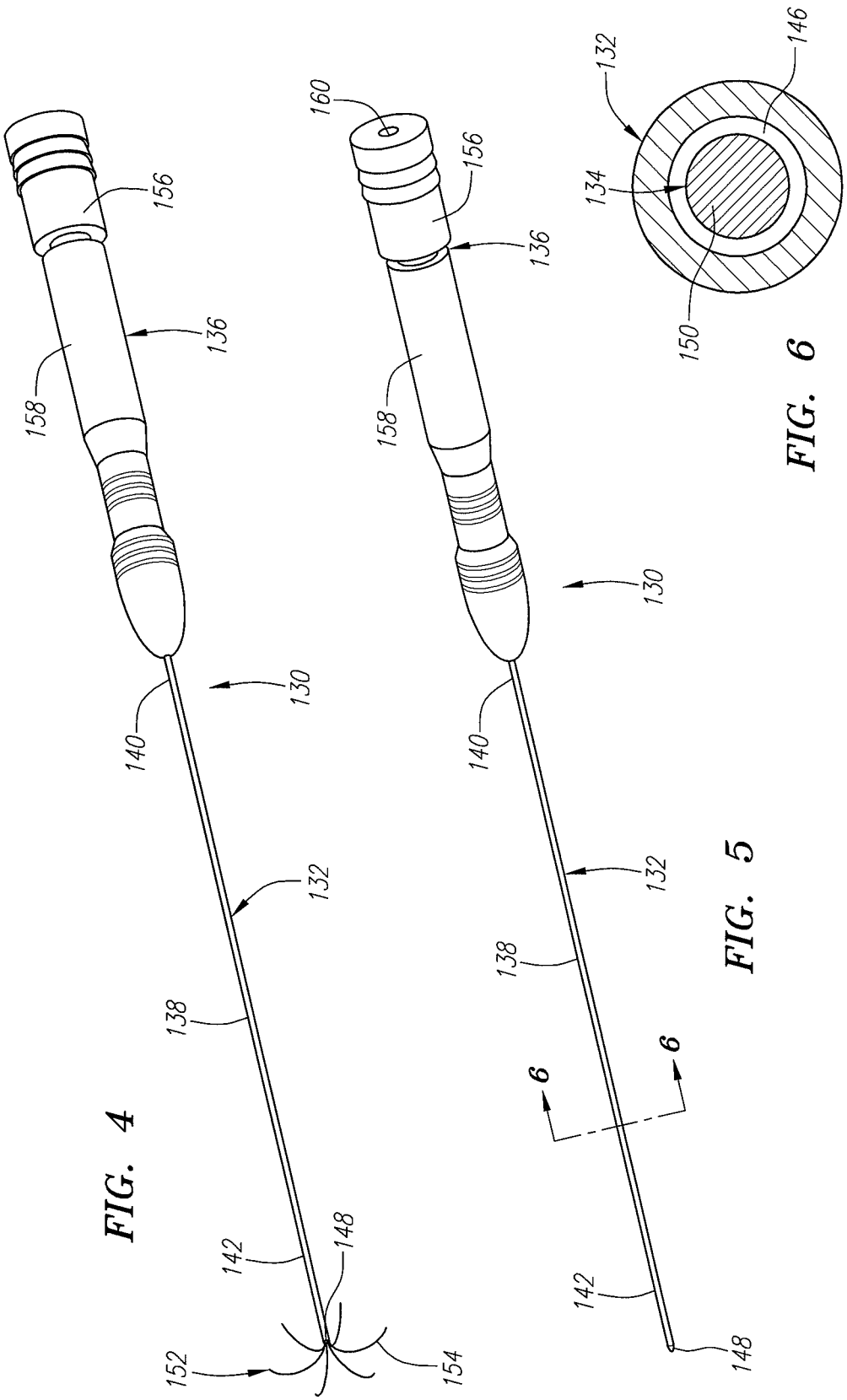

CO-ACCESS FOAM/ELECTRODE INTRODUCER

FIELD OF THE INVENTION

The field of the invention relates generally to the structure and use of radio frequency (RF) electrosurgical devices for the treatment of tissue, and in particular, to the RF ablative treatment of tissue margins surrounding excised interstitial spaces.

BACKGROUND

Tumors and other abnormal tissues can be treated in any one of a variety of manners. In one method, a tumor can be removed from the afflicted patient by retrieving the tumor from the surrounding tissue. For example, breast cancer, if not in an advanced stage that would otherwise require a radical mastectomy (i.e., complete removal of the breast), can be treated using a breast conserving surgical procedure, such as lumpectomy, tumorectomy, segmental mastectomy, or local excision, which involves removal of the suspect tissue and a margin of healthy tissue surrounding the suspect tissue through an open or keyhole incision. In some cases, breast tumors may be removed during a biopsy procedure, e.g., using a tissue retrieval device, such as that described in U.S. Pat. No. 6,471,659.

In any case, the excised interstitial space, which is left behind after removal of the tissue, is typically treated under the theory that a thin finite layer of cells contained within the tissue margin surrounding the interstitial space may be diseased, yet undetectable under the current range of technology, and that even a single malignant cell left in the margins of an excised interstitial space can multiply into a new tumor. Treatment of the margins of the interstitial space is key in reducing the recurrence rate of the disease.

Conventional techniques involving the post-operative treatment of the interstitial space include radiation, chemotherapy, and brachytherapy. Although general ionic radiation treatment utilizes equipment that is commonly available, it must be administered as multiple treatments over a period of weeks, and sometimes months. As a result, general radiation treatment is logistically challenging, time consuming, and costly. In addition, healthy tissue outside of the targeted zone is typically damaged during the radiation process. Focused external beam radiation therapy can be administered to minimize adverse affects to the surrounding healthy tissue. However, external beam radiation therapy utilizes less common equipment, which is typically costly, difficult to find, and/or filled to capacity.

Chemotherapy involves treating the interstitial space with toxic chemotherapeutic agents to destroy any remaining malignant cells. Due to the extreme toxicity of chemotherapeutic agents and variability in the size of the margin, however, chemotherapeutic treatment of an excised interstitial space will lead to the destruction of many healthy, and sometimes critical, cells. Also, due to the large size of the interstitial space relative to areas requiring treatment, it is difficult to obtain predictive infusion of a drug. Furthermore, filling an excised interstitial space results in the use of an excess quantity of the chemotherapeutic agent, which increases the cost of treatment. Increasing the dose of chemotherapeutic agent also increases the amount of the agent absorbed into a patient's system, making it difficult to achieve a therapeutic concentration of a drug locally at a target site within the excised interstitial space without producing unwanted systemic side effects.

Standard brachytherapy techniques require simultaneous placement of numerous catheters in the interstitial space and surrounding tissue. Placement of these catheters can be costly, cumbersome, and time-consuming. New brachytherapy methods, such as the Mammosite® Radiation Therapy System (RTS), use a balloon to deliver a conformal dose of radiation to the tissue over a treatment span of five days. To uniformly radiate the tissue margin around the interstitial space, however, it must be ensured that the balloon contacts the entirety of the wall surrounding the interstitial space. Also, even though the new brachytherapy methods focus therapy in the targeted regions, the use of radiation still poses a danger and is relatively expensive.

It has also been proposed to ablate the wall surrounding the interstitial space using a radio frequency (RF) ablation probe, which would require relatively inexpensive and conventional equipment. The use of RF electrical energy to ablate tissue also has little side effects. However, because RF electrical energy will not ablate tissue in air, the use of RF electrodes in interstitial spaces is ineffective.

For this reason, it would be desirable to provide improved methods and systems for treating interstitial spaces after abnormal tissue, such as a tumor, is excised from a patient.

SUMMARY OF THE INVENTION

In accordance with a first a first aspect of the present inventions, a method of treating a tissue region within a patient, e.g., a margin of tissue surrounding an interstitial space created by removing abnormal tissue, is provided. The method comprises introducing a delivery cannula within the patient. If an interstitial cavity is to be created, a tissue removal device can be advanced through the cannula and operated to remove the tissue. The method further comprises advancing a hydrophilic electrode through the cannula adjacent the tissue region, e.g., within the interstitial cavity. For example, the hydrophilic electrode may be advanced through the cannula by pushing the hydrophilic electrode with a plunger.

The method also comprises exposing the hydrophilic electrode to an electrically conductive liquid, for example, by conveying the electrically conductive liquid through the cannula, whereby the hydrophilic electrode absorbs the electrically conductive liquid. In one method, the hydrophilic electrode is composed of an electrically insulative material, e.g., foam, and the absorbed electrically conductive liquid provides an electrically conductive path through the hydrophilic electrode. The hydrophilic electrode preferably absorbs as much liquid as possible, e.g., an amount equal to at least a dry weight of the hydrophilic electrode.

The method further comprises separately advancing a probe, such as an ablation probe, through the cannula adjacent the hydrophilic electrode, and conveying electrical energy, e.g., radio frequency (RF) energy, from the ablation probe to the hydrophilic electrode, thereby treating the tissue region. The method may optionally comprise deploying at least one electrode from the ablation probe into the hydrophilic electrode prior to conveying electrical energy from the ablation probe to the hydrophilic electrode. Thus, it can be appreciated that the hydrophilic electrode provides a medium through which electrical energy can be conveyed from ablation probe into the surrounding tissue region.

In the case where the tissue margin surrounding an interstitial cavity is to be treated, the hydrophilic electrode may be compressed when delivered through the cannula, and then expanded into contact with the tissue margin when delivered out of the cannula. The hydrophilic electrode may advantageously fill the interstitial cavity. The hydrophilic electrode may self-expand when the compression force of the cannula is released and/or expand upon absorption of the electrically conductive liquid. Thus, electrical energy conveyed from the probe into the expanded hydrophilic electrode may ablate the tissue margin.

In accordance with a second aspect of the present inventions, a medical probe kit is provided. The medical probe kit comprises a delivery cannula having a shaft and a lumen extending through the cannula shaft, and a hydrophilic electrode configured for passing through the cannula lumen. In one embodiment, the hydrophilic electrode is composed of an electrically insulative material, e.g., foam, and is configured for absorbing electrically conductive liquid, e.g., liquid introduced via an optional fluid inlet port located on the cannula, to provide an electrically conductive path through the hydrophilic electrode. The hydrophilic electrode preferably absorbs as much liquid as possible, e.g., an amount equal to at least a dry weight of the hydrophilic electrode. The hydrophilic electrode may optionally comprise a compressed geometry that allows it to pass through the cannula lumen, and an expanded geometry when residing outside of the cannula lumen.

The kit further comprises an ablation probe, e.g., an RF ablation probe, separate from the hydrophilic electrode. The ablation probe is configured for being removably disposed within the cannula lumen, so that a distal end of the ablation probe distally extends from the cannula shaft. The ablation probe may optionally comprise at least one deployable electrode. The medical probe kit may optionally comprise a plunger configured for being removably disposed within the cannula lumen to advance the hydrophilic electrode through and out of the cannula lumen. The medical probe kit may further optionally comprise a tissue removal device configured for being removably disposed within the cannula lumen.

Other and further aspects and features of the invention will be evident from reading the following detailed description of the preferred embodiments, which are intended to illustrate, not limit, the present inventions.

BRIEF DESCRIPTION OF DRAWINGS

The drawings illustrate the design and utility of embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which:

FIG. 4 is a perspective view of an alternative tissue ablation probe that can be used in the tissue treatment system of FIG. 1, particularly showing a deployed electrode array;

FIG. 5 is a perspective view of the tissue ablation probe, particularly showing a retracted electrode array;

FIG. 6 is a cross-sectional view of the tissue ablation probe, taken along the line 6-6;

DETAILED DESCRIPTION OF THE ILLUSTRATED EMBODIMENTS

Figure 1:
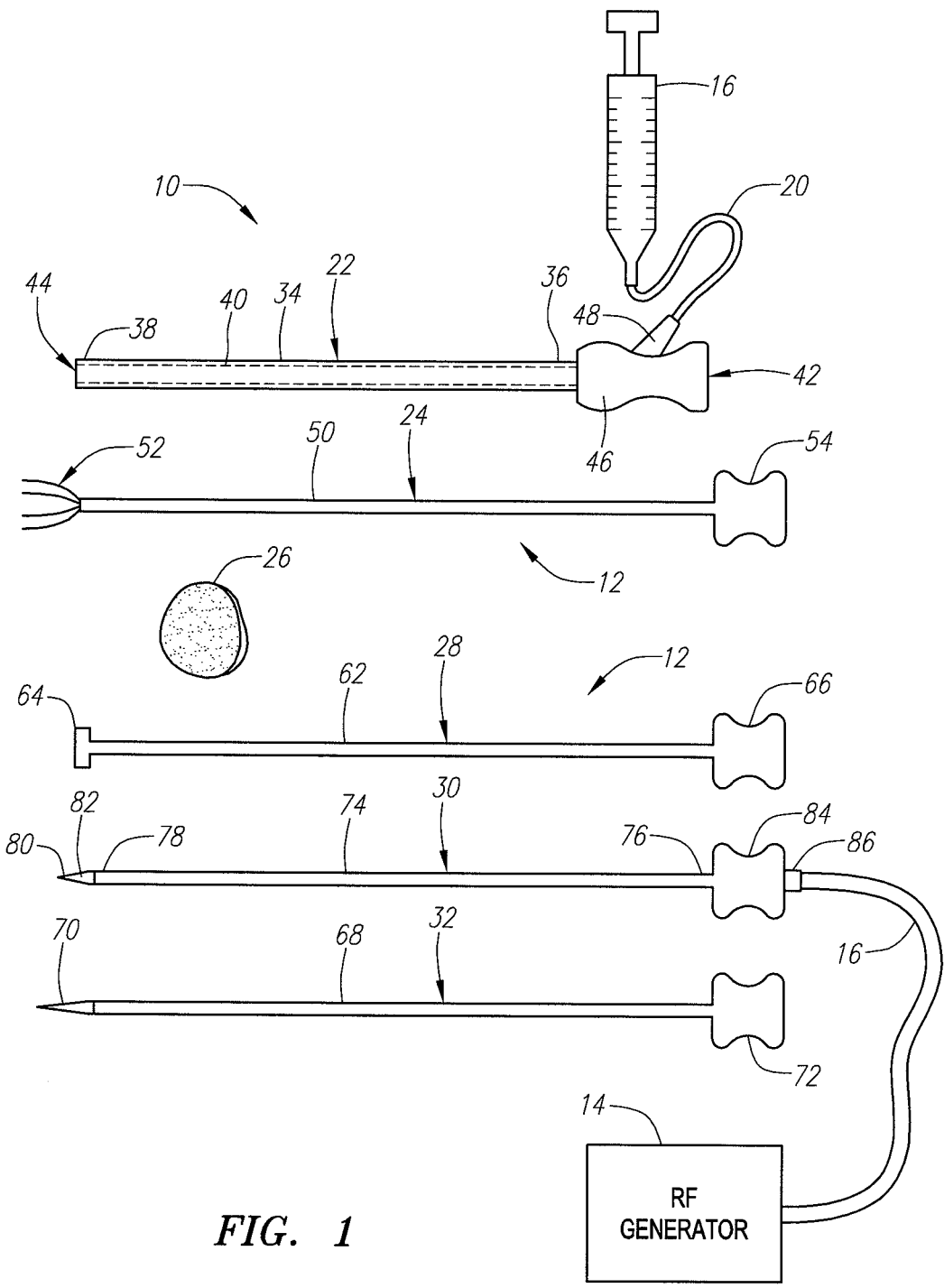
FIG. 1 is a plan view of a tissue treatment system constructed in accordance with a preferred embodiment of the present invention.

Referring to FIG. 1, a tissue treatment system 10 constructed in accordance with an embodiment of the present invention will now be described. The tissue treatment system 10 generally comprises a co-access probe kit 12 configured for introduction into the body of a patient for ablative treatment of target tissue, a tissue ablation source, and in particular a radio frequency (RF) generator 14 configured for supplying RF energy to the tissue ablative component of the probe kit 12 via an RF cable 16 in a controlled manner; and a source of an electrically conductive liquid 18 configured for perfusing liquid, such as saline, through the delivery component of the co-access probe kit 12 via a conduit 20, so that a more efficient and effective ablation treatment is effected.

The co-access probe kit 12 generally comprises (1) a delivery cannula 22 that can be percutaneously introduced within a patient; (2) a tissue removal probe 24 configured for removing tissue from the patient; (3) an expandable hydrophilic electrode 26 configured for absorbing an electrically conductive liquid and conveying RF energy to surrounding tissue; (4) a plunger 28 for advancing the hydrophilic electrode 26 through and out of the delivery cannula 22; and (5) an ablation probe 30 configured for therapeutically ablating tissue. The co-access kit 12 may optionally comprise an obturator 32, such as a trocar, configured for facilitating the percutaneous introduction of the delivery cannula 22 into the patient's body. The tissue removal probe 24, plunger 28, ablation probe 30, and obturator 32 are configured to be interchangeably introduced through the delivery cannula 22 to effect various functions related to the tissue to be treated.

The delivery cannula 22 comprises a cannula shaft 34 having a proximal end 36 and a distal end 38, and a delivery lumen 40 (shown in phantom) extending through the cannula shaft 34. As will be described in further detail below, the cannula shaft 34 may be rigid, semi-rigid, or flexible, depending upon the designed means for introducing the delivery cannula 22 to the target tissue. As will be described in further detail below, the optional obturator 32, or alternatively the ablation probe 30, can be used to facilitate the percutaneous introduction of the delivery cannula 22, which is illustrated with a blunt distal end. The delivery lumen 40 of the cannula 22 proximal begins with an entry delivery port 48 and terminates at an exit delivery port 44 located at the distal tip of the cannula shaft 34. As will be described in further detail below, the exit delivery port 44 serves as a port out which the hydrophilic electrode 26, respective operative elements of the tissue removal probe 24 and ablation probe 30, as well as any liquids and/or chemotherapeutic agents, are delivered to a targeted tissue region.

In the preferred embodiment, the cannula shaft 34 is composed of an electrically conductive material, such as stainless steel. In this case, the exterior surface of the cannula shaft 34 is preferably composed of an electrically insulative material. Alternatively, the cannula shaft 34 may be composed of an electrically insulative material, such as a medical grade plastic, in which case, a separate insulative coating is not needed. The cannula shaft 34 has a suitable length, typically in the range from 5 cm to 30 cm, preferably from 10 cm to 20 cm, an outside diameter consistent with its intended use, typically being from 1 mm to 5 mm, usually from 1.3 mm to 4 mm, and an inner diameter typically being from 0.7 mm to 4 mm, preferably from 1 mm to 3.5 mm.

The delivery cannula 22 further comprises a handle 46 mounted to the proximal end 36 of the cannula shaft 34. The handle 46 is preferably composed of a durable and rigid material, such as medical grade plastic, and is ergonomically molded to allow a physician to more easily manipulate the cannula 22. The cannula 22 further comprises a fluid inlet port 48 located on the handle 46, so that the delivery cannula 22 can be used to deliver liquids, such as an electrically conductive liquid or chemotherapeutic agents to tissue.

Referring still to FIG. 1, the tissue removal probe 24 may be a conventional percutaneous tissue removal device (such as the En-bloc tumor removal assembly marketed by Neothermia or the MiniTome Potential marketed by Artemis), which can be used to remove a tissue sample and/or completely remove an abnormality. To this end, the tissue removal probe 24 comprises a solid elongated shaft 50 with a distal tissue grabbing mechanism 52 and a proximal handle piece 54. The handle piece 54 is preferably composed of a durable and rigid material, such as medical grade plastic, and may be shaped to mate with the handle 46 of the cannula 22 to form an integrated handle assembly. The tissue removal probe 24 may optionally be vacuum-assisted to aspirate tissue.

Figure 2:
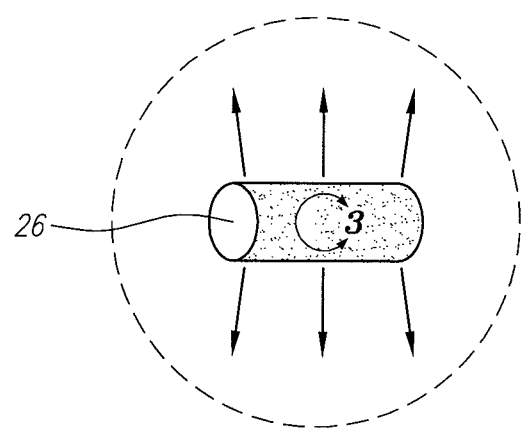
FIG. 2 is a perspective view of a hydrophilic electrode used in the tissue treatment system of FIG. 1.

As illustrated in FIG. 2, the electrode 26 is composed of biocompatible compressible/expandable material that allows the electrode 26 to be alternately compressed, so that it can be housed within the relatively small profile cannula lumen 40, and expanded (shown in phantom), so that it can substantially fill a void, such as an interstitial cavity, when deployed from the delivery lumen 40 of the cannula 22. In the illustrated embodiment, the electrode 26 is self-expanding in that it automatically expands from its compressed state immediately upon the release of a compressive force.

Figure 3:
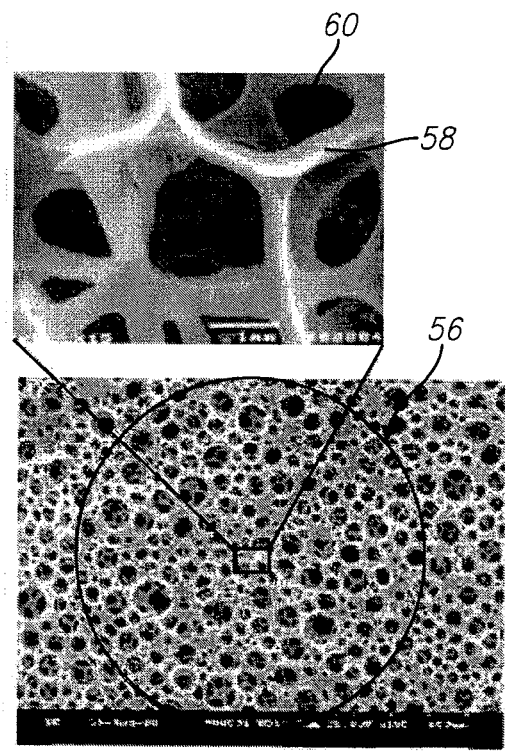
FIG. 3 is a magnified view of the hydrophilic electrode of FIG. 2, taken along line 3-3.

To this end, as illustrated in FIG. 3, the compressible/expandable material comprises a skeletal structure 56 formed of elements 58 that collapse within spaces 60 between the elements 58 upon the application of a compressive force and expand upon the release of the compressive force. Preferably, the elements 58 are as thin as possible to maximize the expandability/compressibility ratio of the electrode 26, i.e., the volume of the electrode 26 in its expanded form divided by the volume of the electrode 26 in its compressed form. In this manner, the size of the delivery lumen 40 of the cannula 22, and thus the cannula 22, can be minimized as much as possible, while ensuring that the electrode 26 fills the interstitial cavity when expanded. In a preferred embodiment, the electrode 26 preferably has an expandability/compressibility ratio of more than one, preferably more than two, and most preferably more than five. The electrode 26 may also be composed of a material that expands the electrode 26 in additional volume in response absorption of the liquid. In this manner, the effective expandability/compressibility ratio of the electrode 26 is further increased.

The electrode 26 may be sized and shaped in accordance with the interstitial cavity. In the illustrated embodiment, the expanded electrode 26 is spherically-shaped. Other shapes, such as ellipsoidal, can be used, depending on the shape of the interstitial cavity. However, since the electrode 26 is preferably composed of a material that has a relatively high compliancy (i.e., it is highly compressible), any one electrode will naturally assume the shape of any variety of differently shaped interstitial cavities when expanded. Suitable expanded sizes may fall in the range of 0.5-8.0 cm, and preferably within the range of 2.0-5 cm.

The electrode 26 is hydrophilic in that it is capable of absorbing a substantial amount of liquid. It is preferred that the material used in the electrode 26 be capable of absorbing an amount of liquid at least equal to its dry weight, preferably an amount at least equal to at least two times its dry weight, and more preferably an amount at least equal to at least four times its dry weight. In general, the more liquid absorbed per unit dry weight of the electrode 26, the more electrically conductive the electrode 26 will be. To this end, the ratio between the volume of the spaces 60 and the volume of the elements 58 is maximized.

Suitable materials that can be used to construct the electrode 26 include open-cell foam (such as polyethylene foam, polyurethane foam, polyvinylchloride foam) and medical-grade sponges. In the illustrated embodiment, a foam composed of Hypol 3000 base polymer marketed by W.R. Grace & Co, an L-62 Surfactant marketed by BASF Corporation, and water is used. It has been found that the open-cell polyurethane foam marketed by Avitar, Inc. as Hydrosorb™ is especially suitable, and has been found to have an expandability/compressibility ratio of 10:1, and be capable of absorbing an amount of liquid twenty times its weight. In addition, it has been found that the use of Hydrosorb™ allows the electrode 26 to expand to 125-130% of its original uncompressed size, thereby facilitating conformance of the electrode 26 within the interstitial cavity, and thus, uniform firm contact between the electrode 26 and the tissue margin. Polyvinyl acetal sponges, such as Merocel™, marketed by Medtronic, Inc., and cellulose sponges, such as Weckcel™ are also suitable. It should be appreciated that material, other than foam or sponges may be used for the electrode 26 as long as it is capable of absorbing a sufficient amount of liquid and expands to a size necessary to fill the interstitial cavity to be treated. For example, spun-laced polyester, cotton, gauze, cellulose fiber, or the like can be used. It can be appreciated that although suitable materials used in the electrode 26 will typically be electrically insulative, the electrode 26 will become electrically conductive upon absorption of electrically conductive liquid.

For the purpose of delaying absorption of bodily fluids, the electrode 26 may optionally have a bioabsorption coating (not shown) applied to its outer surface, which controls the rate and amount of liquid that enters into the absorbent material of the electrode 26. That is, the bioabsorption coating gradually dissolves upon exposure to bodily fluid at a known rate. In this manner, the electrode 26 will not fully expand until it is desired, i.e., when the electrically conductive liquid is perfused into the electrode 26. In another optional embodiment, the electrode 26 may be impregnated with a chemotherapeutic agent (not shown). In this manner, the tissue margin, in addition to being therapeutically ablated, will be treated with the chemotherapeutic agent.

Referring back to FIG. 1, the plunger 28 is configured for pushing the hydrophilic electrode 26, which will be compressed within the cannula 30, through the delivery lumen 40 of the cannula 22 and out of the exit delivery port 44. To this end, the plunger 28 includes a rigid shaft 62, a distal plunger head 64 sized to snugly fit within the delivery lumen 40 of the cannula 22, and a proximal handle piece 66. The length of the rigid shaft 62, is such that the plunger head 64 extends from the distal end 38 of the cannula shaft 34 when the plunger 28 is fully inserted within the delivery lumen 40 of the cannula 22. Alternatively, the plunger 28 does not include a plunger head, but merely consists of a rigid shaft, the distal end of which is configured to engage the compressed hydrophilic electrode 26. The handle piece 66 is preferably composed of a durable and rigid material, such as medical grade plastic, and may be shaped to mate with the handle 46 of the cannula 22 to form an integrated handle assembly.

The obturator 32 takes the form of a conventional trocar that includes a rigid shaft 68, a distal tissue-penetrating distal tip 70, and a proximal handle piece 72. The length of the rigid shaft 68 is such that the distal tip 70 distally extends from the distal end 38 of the cannula shaft 34 when the obturator 32 is fully inserted within the delivery lumen 40 of the cannula 22. The rigid shaft 68 of the obturator 32 is sized to snugly fit within the delivery lumen 40 of the cannula 22, such that the combination of the cannula 22 and obturator 32 act as a single device when percutaneously introduced through tissue. The handle piece 72 is preferably composed of a durable and rigid material, such as medical grade plastic, and may be shaped to mate with the handle 46 of the cannula 22 to form an integrated handle assembly.

The ablation probe 30 comprises an elongated shaft 74 having a proximal end 76 and a distal end 78. The probe shaft 74 is preferably composed of a rigid or semi-rigid material, such that the probe shaft 74 can be introduced through solid tissue to the target tissue site when deployed from the delivery cannula 22. The distal end 78 of the probe shaft 74 comprises a closed tissue-penetrating tip 80, which allows the cannula 22, in combination with the ablation probe 30, to be more easily introduced through tissue, while preventing tissue coring and minimizing tissue trauma. The probe shaft 74, in the preferred embodiment, is composed of an electrically conductive material, such as stainless steel. Alternatively, the probe shaft 74 may be composed of an electrically insulative material, such as a medical grade plastic, in which case, a separate insulative coating is not needed.

The probe shaft 74 has a suitable length that is slightly longer than the length of the cannula shaft 34, so that the distal tip 80 of the probe shaft 74 extends from the distal end 38 of the cannula shaft 34 when the ablation probe 30 is completely introduced into the delivery lumen 40 of the cannula 22. The probe shaft 74 has an outer diameter that conforms with the inner diameter of the cannula shaft 34. Preferably, the outer diameter of the probe shaft 74 and the delivery lumen 40 of the cannula shaft 34 are closely toleranced to prevent tissue-coring during the introduction of the cannula 22 and ablation probe 30.

The ablation probe 30 further comprises an RF ablation electrode 82 carried by the distal end 78 of the probe shaft 74. In this case wherein the probe shaft 74 is composed of an electrically conductive material, the exterior surface of the probe shaft 74, with the exception of the distal tip 80, is preferably composed of an electrically insulative material (not shown), thereby forming the electrode 82 at the exposed portion of the shaft distal tip 80. Alternatively, if the probe shaft 74 is composed of an electrically insulative material, the distal tip 80 can be coated with an electrically conductive material to form the electrode 82 thereon, or a discrete ring electrode can be interference fit at the base of the distal tip 80. In this alternative case, a separate RF wire (not shown) can be routed from the electrode 82 back through a lumen (not shown) within the probe shaft 74.

The ablation probe 30 further comprises a handle piece 84 mounted to the proximal end 76 of the probe shaft 74. The handle 66 is preferably composed of a durable and rigid material, such as medical grade plastic, and may be shaped to mate with the handle 46 of the cannula 22 to form an integrated handle assembly. The ablation probe 30 further comprises an electrical connector 86 incorporated into the handle piece 84 with which the RF cable 16 mates. The electrical connector 86 is electrically coupled to the ablation electrode 82 via the probe shaft 74, or alternatively via RF wires (not shown).

Referring now to FIGS. 4 and 5, another tissue ablation probe 130 that can be used in conjunction with the RF generator 14 to create an alternative tissue treatment system will be described. The ablation probe 130 generally comprises an elongated cannula 132, an inner probe 134 (shown in FIG. 6) slideably disposed within the cannula 132, and a handle assembly 136. As will be described in further detail below, the cannula 132 serves to deliver the active portion of the inner probe 134 to the target tissue.

The cannula 132 includes an elongate shaft 138 having a proximal end 142 and a distal end 144, and a central lumen 146 (shown in FIG. 6) extending through the cannula shaft 138. The material from which the cannula shaft 138 is composed is preferably a rigid or semi-rigid material, such that the ablation probe 130 can be introduced through solid tissue to a target tissue site in conjunction with the delivery cannula 132. To this end, the distal end 144 of the cannula shaft 138 comprises a tissue-penetrating tip 148, which allows the ablation probe 130 to be more easily introduced through tissue, while minimizing tissue trauma.

The inner probe 134 comprises a reciprocating shaft 150 (shown in FIG. 6) and an array 152 of tissue penetrating needle electrodes 154 extending from the distal end of the shaft 138. Like the cannula shaft 138, the inner probe shaft 150 is rigid and is composed of a suitable material, such as plastic or metal. Alternatively, the inner probe shaft 150 can be composed of a semi-rigid material, such as, e.g., stainless steel braid, that when radially constrained by the inner surface of the cannula shaft 138, provides the necessary columnar strength for the inner probe 134 to be distally pushed within the cannula lumen 146.

The handle assembly 136 includes a handle member 156 mounted to the proximal end of the inner probe shaft 150, and a handle sleeve 158 mounted to the proximal end 142 of the cannula shaft 138. The handle member 156 is slidably engaged with the handle sleeve 158 (and the cannula 132). The handle member 156 and handle sleeve 158 can be composed of a durable and rigid material, such as medical grade plastic, and may be shaped to mate with the handle 46 of the cannula 22 to form an integrated handle assembly. The handle assembly 136 also includes an electrical connector 160 mounted within the handle member 104. The electrical connector 160 is electrically coupled to the electrode array 152 via the inner probe shaft 150, and is configured for mating with the RF cable 16.

It can be appreciated that longitudinal translation of the probe shaft 138 relative to the cannula 132 in a distal direction can be achieved by holding the handle sleeve 106 and displacing the handle member 104 in the distal direction, thereby deploying the electrode array 152 from the distal end 144 of the cannula shaft 138 (FIG. 4), and longitudinal translation of the probe shaft 138 relative to the cannula 132 in a proximal direction can be achieved by holding the handle sleeve 106 and displacing the handle member 104 in the proximal direction, thereby retracting the probe shaft 138 and the electrode array 152 into the distal end 144 of the cannula shaft 88 (FIG. 5).

Further details regarding electrode array-type probe arrangements are disclosed in U.S. Pat. No. 6,379,353, which is hereby expressly incorporated by reference.

Referring back to FIG. 1, the RF generator 104 is electrically connected to the electrical connector 86 of the ablation probe 30, or alternatively, the electrical connector 160 of the ablation probe 130, via the cable 16. The RF generator 104 may be a conventional RF power supply that operates at a frequency in the range from 300 KHz to 9.5 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for tissue ablation. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., who markets these power supplies under the trademarks RF2000 (100 W) and RF3000 (200 W).

In the illustrated embodiment, RF current is delivered from the RF generator 104 to the electrode 82, or alternatively the electrode array 152, in a monopolar fashion, which means that current will pass from the electrode 82 (or electrode array 152), which is configured to concentrate the energy flux in order to have an injurious effect on the surrounding tissue, and a dispersive electrode (not shown), which is located remotely from the electrode 82 (or electrode array 152) and has a sufficiently large area (typically 130 $cm^2$ for an adult), so that the current density is low and non-injurious to surrounding tissue. In the illustrated embodiment, the dispersive electrode may be attached externally to the patient, e.g., using a contact pad placed on the patient's flank.

In the illustrated embodiment, the fluid source 16 takes the form of a syringe connected to the fluid inlet port 48 of the cannula 22 via the conduit 20. The syringe 16 contains an electrically conductive liquid, such as saline. The syringe 16 is conventional and is of a suitable size, e.g., 200 ml. In the illustrated embodiment, the electrically conductive liquid is 0.9% saline. Thus, it can be appreciated the syringe 16 can be operated to convey the saline through the tubing?, into the fluid inlet port 48, through the delivery lumen 40 of the cannula 22, and out of the axial opening 38. Alternatively, rather than a syringe, the fluid source 16 may take the form of a pump assembly or a saline bag raised above the patient a sufficient height to provide the head pressure necessary to convey the fluid under pressure.

Having described the structure of the tissue treatment system 10 in treating targeted tissue will now be described. Although the tissue treatment system 10 lends itself well to the treatment of tumors within breast tissue, the tissue treatment system 10 may be used to treat targeted tissue located anywhere in the body where hyperthermic exposure may be beneficial, e.g., within an organ of the body, such as the liver, kidney, pancreas, prostrate (not accessed via the urethra), and the like. The volume to be treated will depend on the size of the tumor or other lesion, typically having a total volume from 1 $cm^3$ to 150 $cm^3$, and often from 2 $cm^3$ to 35 $cm^3$. The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 7A:
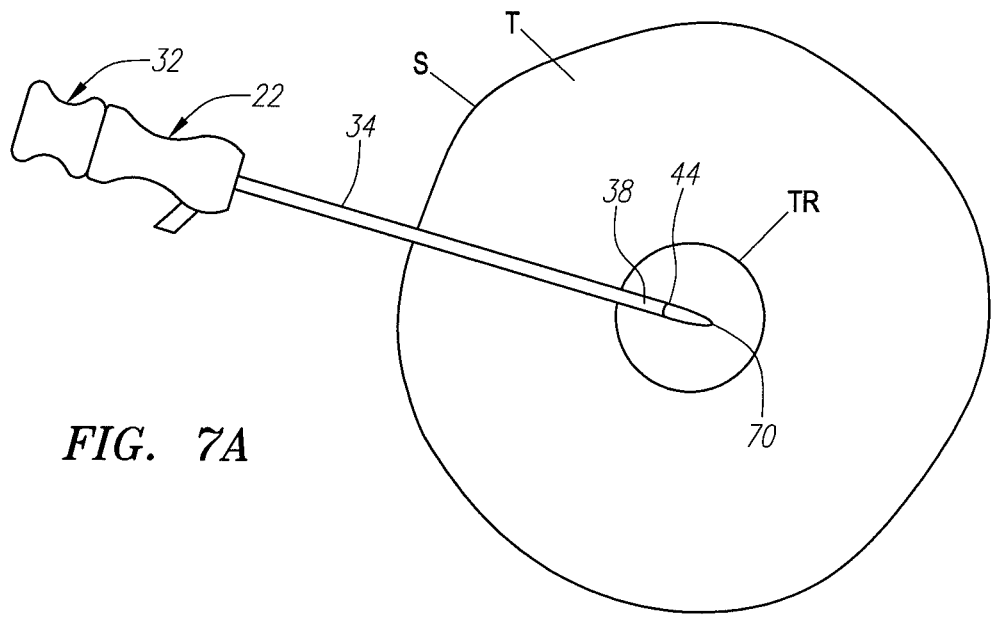
FIGS. 7A-7H are side views illustrating a method of treating tissue with the tissue treatment system of FIG. 1.

Referring to FIGS. 7A-7H, the operation of the tissue treatment system 10 is described in treating a target region TR within T located beneath the skin or an organ surface S of a patient. The delivery cannula 22 is first introduced through the tissue T, so that the distal end 38 of the cannula shaft 34 is located at the target region TR, as shown in FIG. 7A. This can be accomplished using any one of a variety of techniques. In the preferred method, the optional obturator 32 is introduced into the delivery lumen 40 of the cannula 22, and then the cannula 22 with the obturator 32, is introduced to the treatment region TR percutaneously directly through the patient's skin or through an open surgical incision. In this case, the sharpened tip 70 of the obturator 32, which will extend out from the exit delivery port 44 at the distal end 38 of the cannula shaft 34, facilitates introduction to the treatment region TR. Alternatively, the ablation probe 46 can be introduced into the delivery lumen 40 of the cannula 22, in which case, the cannula 22 with the distal tip 80 of the ablation probe 46 extending therefrom, can be introduced to the treatment region TR. The sharpened distal tip 80 of the ablation probe 46 facilitates introduction to the treatment region TR in this case. Because the ablation probe 30 and obturator 32 are sufficiently rigid, i.e., have a sufficient column strength, the cannula 22 need not be rigid, but instead can be flexible if desired. In any event, the cannula 22 can be properly positioned relative to the treatment region TR under ultrasonic or other conventional imaging.

Figure 7B:
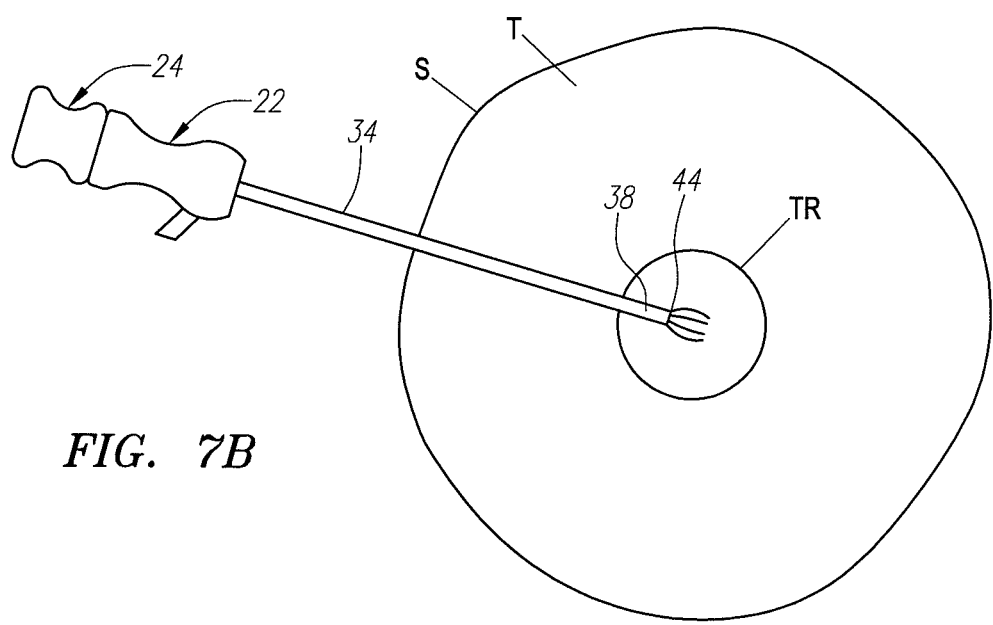
Figure 7C:
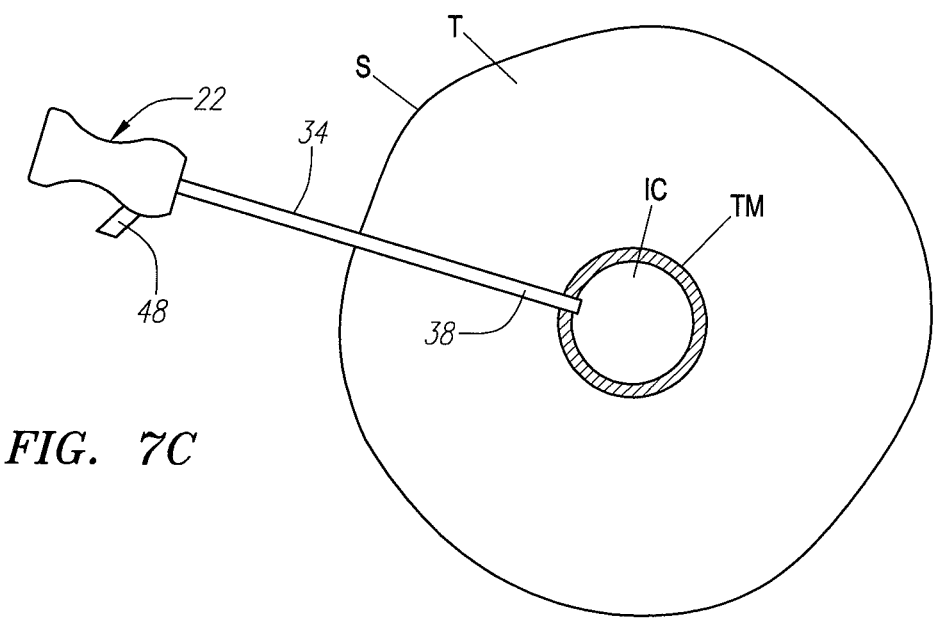
Figure 7D:
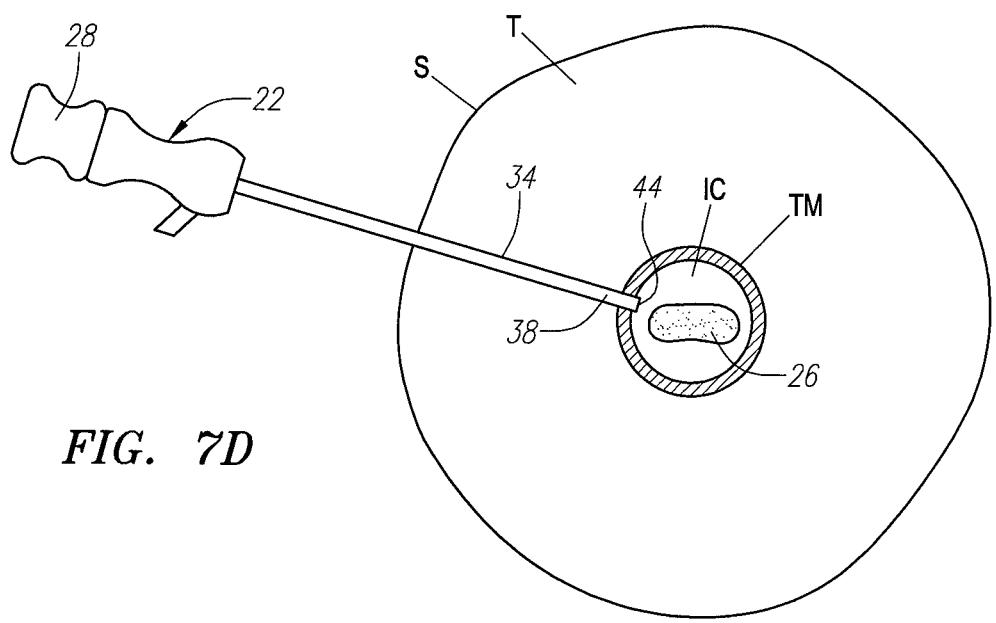

Next, the obturator 32 or ablation probe 46 is exchanged for the ablation tissue removal device 24. In particular, the obturator 32 or ablation probe 46 is removed from the delivery lumen 40 of the cannula 22, and then the tissue removal device 24 is introduced into the delivery lumen 40, so that the tissue grabbing mechanism 52 extends out of the exit delivery port 44 at the distal end 38 of the cannula shaft 34 (FIG. 7B). The tissue removal device 24 is then operated in a conventional manner to remove the tumor T from the patient, and then the device 24 is removed from the delivery lumen 40 of the cannula 22, thereby creating an interstitial cavity IC surrounding by a tissue margin TM (FIG. 7C). Next, the hydrophilic electrode 26, in its compressed geometry, is inserted into the delivery lumen 40 of the cannula 22, and the plunger 28 is advanced through the delivery lumen 40 to push the compressed hydrophilic electrode 26 through the delivery lumen 40, out of the exit delivery port 44 at the distal end 38 of the cannula shaft 34, and into the interstitial cavity IC (FIG. 7D). Depending upon the architecture and composition of the hydrophilic electrode 26, the electrode 26 may partially or completely self-expand upon its deployment from the cannula 22, or may remain in its compressed state. In the illustrated method, the hydrophilic electrode 26 is shown partially expanded, so that it only partially fills the entire interstitial cavity IC.

Figure 7E:
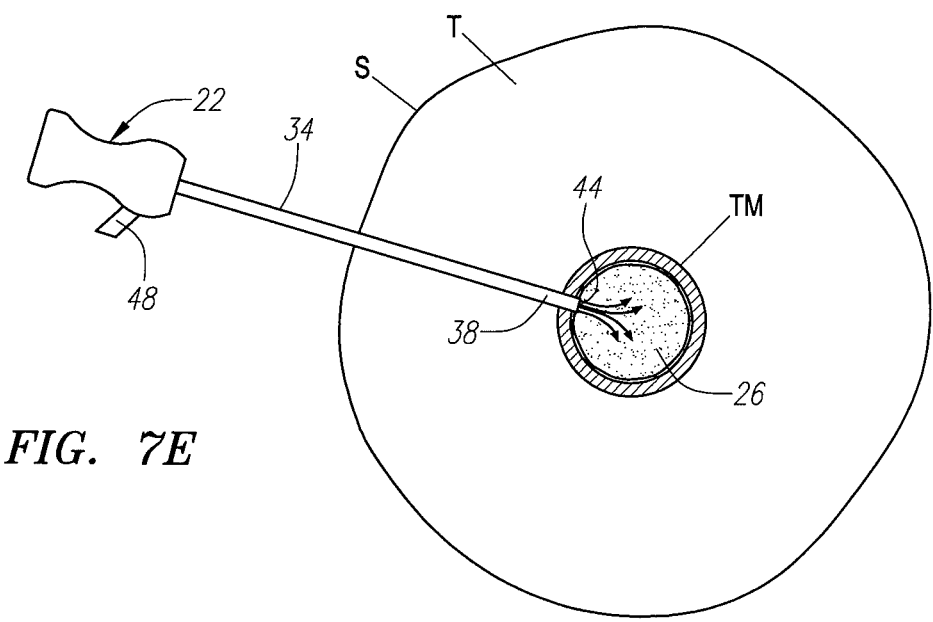

Next, after the plunger 24 is removed from the delivery lumen 40 of the cannula 22, the syringe 16 and associated conduit 20 (shown in FIG. 1) are connected to the fluid inlet port 48 on the cannula 22, and the syringe 16 operated, such that the saline is conveyed under positive pressure, through the conduit 20, through the delivery lumen 40 of the cannula 22, and out of the exit delivery port 44 (shown by arrows) into contact with the hydrophilic electrode 26, where it is absorbed by the electrode 26. As a result, the hydrophilic electrode 26 becomes electrically conductive, and if not completely expanded already, will expand into firm and uniform contact with the tissue margin TM (FIG. 7E). Notably, even if the shape of the expanded electrode 26 does not match the shape of the interstitial cavity IC, the pliability of the electrode 26 allows it to easily conform to the tissue margin TM.

Figure 7F:
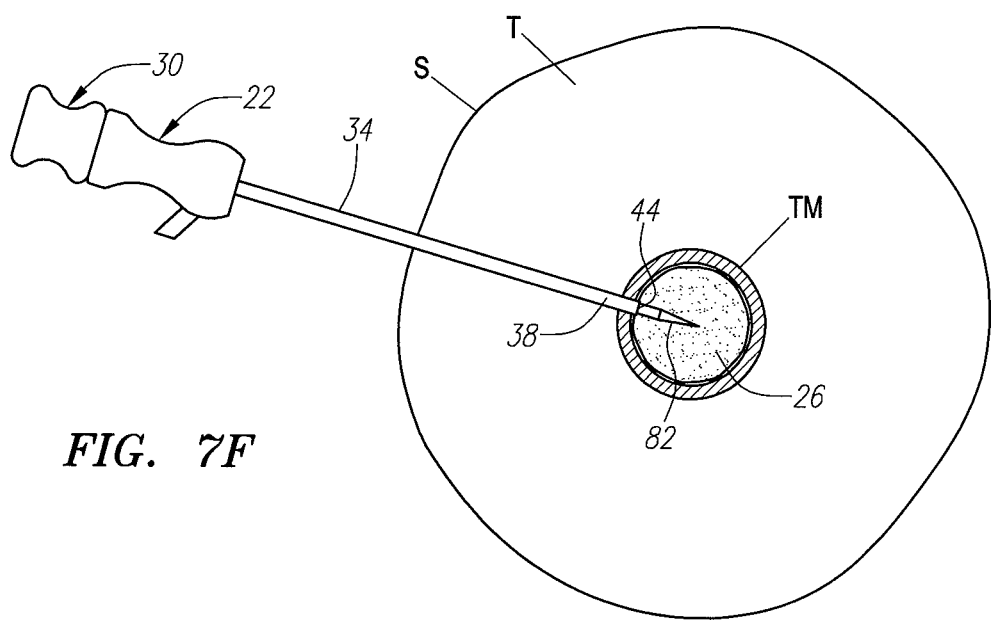
Figure 7G:
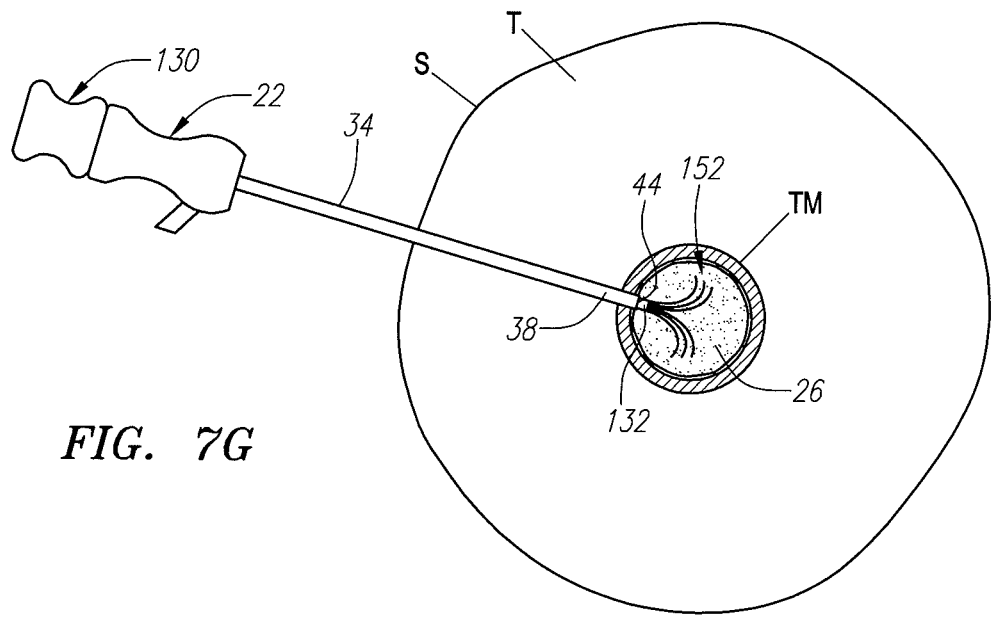

The ablation probe 30 is then introduced through the delivery lumen 40 of the cannula 22 until the electrode 82 of the exit delivery port 44 at the distal end 38 of the cannula shaft 34 into contact with, and preferably inserted within, the expanded hydrophilic electrode 26 (FIG. 7F). Alternatively, the ablation probe 30 is introduced through the delivery lumen 40 of the cannula 22, and the electrode array 152 deployed from the cannula 132 of the ablation probe 30, out of the exit delivery port 44 at the distal end 38 of the cannula shaft 34, and into the expanded hydrophilic electrode 26 (FIG. 7G).

Figure 7H:
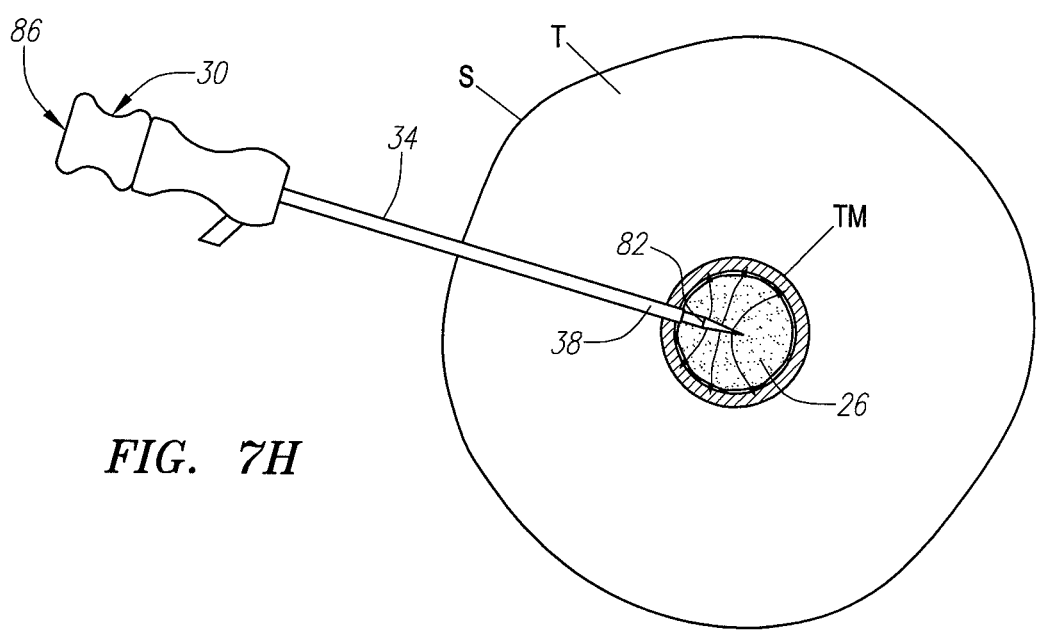

The RF generator 14 and associated RF cable 16 (shown in FIG. 1) are connected to the electrical connector 86 of the ablation probe 30 (or alternatively, the electrical connector 160 on the ablation probe 130), and then operated. As a result, electrical energy (shown by arrows) is conveyed from the electrode 82 (or electrode array 152) into the hydrophilic electrode 26, which the electrical energy is, in turn, uniformly conveyed to the tissue margin TM (FIG. 7H). If the hydrophilic electrode 26 is impregnated with a chemotherapeutic agent, any gaseous substances created as a result of the thermal ablation process will escape from the interstitial cavity IC outward through the tissue margin TM, thereby carrying the chemotherapeutic agent with it into the tissue margin TM where chemotherapy is needed. Thus, any pathological agents not otherwise killed by the ablation process will be killed by the chemotherapy. It should also be noted that the heat created by the thermal ablation process increases the metabolic process of the tissue margin TM, thereby facilitating uptake of the chemotherapeutic agent within the tissue.

Optionally, after the ablation probe 30 (or ablation probe 130) is removed from the delivery lumen 40 of the cannula 22, a liquid chemotherapeutic agent can be introduced into the fluid inlet port 48, through the delivery lumen 40, out of the exit delivery port 44, and into the already ablated tissue margin TM. The cannula 22 may then be removed from the patient.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed:

1. A method of treating a margin of tissue surrounding an interstitial space within a patient, comprising:
   introducing a delivery cannula within the patient;
   advancing a hydrophilic electrode in a compressed state through the cannula and into the interstitial space by pushing the hydrophilic electrode with a plunger, the hydrophilic electrode comprising a self-expanding material;
   removing the plunger away from direct contact with the hydrophilic electrode and leaving the hydrophilic electrode in the interstitial space so as to expand and substantially fill the interstitial space, wherein said expansion occurs upon release of a compressive force applied by the cannula;
   separately advancing an ablation probe through the cannula so that the ablation probe is adjacent the hydrophilic electrode; and
   conveying electrical energy from the ablation probe to the expanded electrode, thereby ablating the tissue margin.

2. The method of claim 1, wherein the hydrophilic electrode is composed of an electrically insulative material, and the absorbed electrically conductive liquid provides an electrically conductive path through the hydrophilic electrode.

3. The method of claim 1, wherein the hydrophilic electrode is composed of a foam material.

4. The method of claim 1, wherein the hydrophilic electrode absorbs an amount of liquid equal to at least a dry weight of the hydrophilic electrode.

5. The method of claim 1, further comprising conveying the electrically conductive liquid through the cannula into contact with the hydrophilic electrode.

6. The method of claim 1, wherein the electrical energy is radio frequency (RF) energy.

7. The method of claim 1, further comprising removing abnormal tissue to create the interstitial space.

8. The method of claim 7, wherein the abnormal tissue removal comprises advancing a tissue removal device through the cannula, and operating the tissue removal device to remove the tissue.

9. The method of claim 1, further comprising deploying at least one electrode from the ablation probe into the hydrophilic electrode prior to conveying electrical energy from the ablation probe to the expanded electrode.

10. The method of claim 1, wherein the hydrophilic electrode has an expandability/compressibility ratio of more than one.

11. The method of claim 1, wherein the hydrophilic electrode has an expandability/compressibility ratio of more than two.

12. The method of claim 1, wherein the hydrophilic electrode has an expandability/compressibility ratio of more than five.

13. A method of treating a tissue region within a patient, comprising:
   introducing a delivery cannula within the patient;
   advancing a hydrophilic electrode through the cannula by pushing the hydrophilic electrode with a plunger until the hydrophilic electrode is adjacent the tissue region;
   removing the plunger away from direct contact with the hydrophilic electrode and leaving the hydrophilic electrode adjacent to the tissue region, wherein the hydrophilic electrode expands upon release of a compressive force applied by the cannula;
   separately advancing a probe through the cannula so that the probe is adjacent the hydrophilic electrode;
   exposing the hydrophilic electrode to an electrically conductive liquid, whereby the hydrophilic electrode absorbs the electrically conductive liquid and the hydrophilic electrode further expands against the tissue region; and
   conveying electrical energy from the probe to the exposed hydrophilic electrode, thereby ablating the tissue region.

14. The method of claim 13, wherein the hydrophilic electrode is composed of an electrically insulative material, and the absorbed electrically conductive liquid provides an electrically conductive path through the hydrophilic electrode.

15. The method of claim 13, wherein the hydrophilic electrode is composed of a foam material.

16. The method of claim 13, wherein the hydrophilic electrode absorbs an amount of liquid equal to at least a dry weight of the hydrophilic electrode.

17. The method of claim 13, further comprising conveying the electrically conductive liquid through the cannula into contact with the hydrophilic electrode.

18. The method of claim 13, wherein the electrical energy is radio frequency (RF) energy that ablates the tissue region.

19. The method of claim 13, further comprising deploying at least one electrode from the probe into the hydrophilic electrode prior to conveying electrical energy from the probe to the exposed electrode.

20. The method of claim 13, wherein the hydrophilic electrode has an expandability/compressibility ratio of more than one.

21. The method of claim 13, wherein the hydrophilic electrode has an expandability/compressibility ratio of more than two.

22. The method of claim 13, wherein the hydrophilic electrode has an expandability/compressibility ratio of more than five.

\* \* \* \* \*